United States Patent
Boillat et al.

(10) Patent No.: US 7,303,728 B2
(45) Date of Patent: Dec. 4, 2007

(54) FLUID DISPENSING DEVICE

(75) Inventors: Marc Boillat, Auvernier (CH); Bart Van Der Schoot, Neuchâtel (CH); Bastien Droz, Cortaillod (CH); Xavier Tinguely, Fontaines (CH)

(73) Assignee: Seyonic SA, Neuchatel (CH)

( * ) Notice: Subject to any disclaimer, the term of this patent is extended or adjusted under 35 U.S.C. 154(b) by 592 days.

(21) Appl. No.: 10/399,583

(22) PCT Filed: Oct. 12, 2001

(86) PCT No.: PCT/CH01/00614

§ 371 (c)(1),
(2), (4) Date: Apr. 18, 2003

(87) PCT Pub. No.: WO02/33423

PCT Pub. Date: Apr. 25, 2002

(65) Prior Publication Data
US 2004/0020938 A1 Feb. 5, 2004

(30) Foreign Application Priority Data
Oct. 20, 2000 (EP) ................... 00810970

(51) Int. Cl.
B01L 3/02 (2006.01)
(52) U.S. Cl. ............... 422/100; 73/863.02; 73/863.03; 73/864.11; 436/180

(58) Field of Classification Search ............... 422/100; 436/180; 73/863.01–863.03, 864.11
See application file for complete search history.

(56) References Cited

U.S. PATENT DOCUMENTS

| | | | |
|---|---|---|---|
| 5,143,849 A | 9/1992 | Barry et al. | 436/50 |
| 5,916,524 A | 6/1999 | Tisone | 422/100 |
| 5,918,291 A | 6/1999 | Inacu et al. | 73/863.83 |
| 5,927,547 A | 7/1999 | Papen et al. | 222/57 |
| 6,190,619 B1 | 2/2001 | Kilcoin et al. | 422/131 |
| 6,203,759 B1 | 3/2001 | Pelc et al. | 422/100 |

FOREIGN PATENT DOCUMENTS

| | | |
|---|---|---|
| EP | 0 505 004 | 9/1992 |
| EP | 0 747 689 | 12/1996 |
| EP | 0 865 824 | 9/1998 |
| WO | WO 98/45025 | 10/1998 |
| WO | WO 99/20395 | 4/1999 |

*Primary Examiner*—Jan M. Ludlow
(74) *Attorney, Agent, or Firm*—Townsend M. Belser, Jr.; Nexsen Pruet Adams Kleemeier, LLC

(57) ABSTRACT

The invention concerns a fluid dispensing device, characterised in that it comprises: a dispensing member (10) including: a conduit (42, 44) allowing through a transporting liquid (52), a valve (48) fixed to one of the ends (38) of said conduit, a dispensing needle (12) arranged at the other end (38), means for measuring the flow rate (46) of the transporting liquid (52) in the conduit, control means (54) for circulating the said liquid through said conduit in one direction or the other, and electronic means (58, 60) reacting to said measuring means (46) and acting both on said valve (48) and said control means (54) to cause a specific amount of fluid (30) to be sucked into the needle (12), and then to be restored.

6 Claims, 2 Drawing Sheets

FLUID DISPENSING DEVICE

Figure 1:
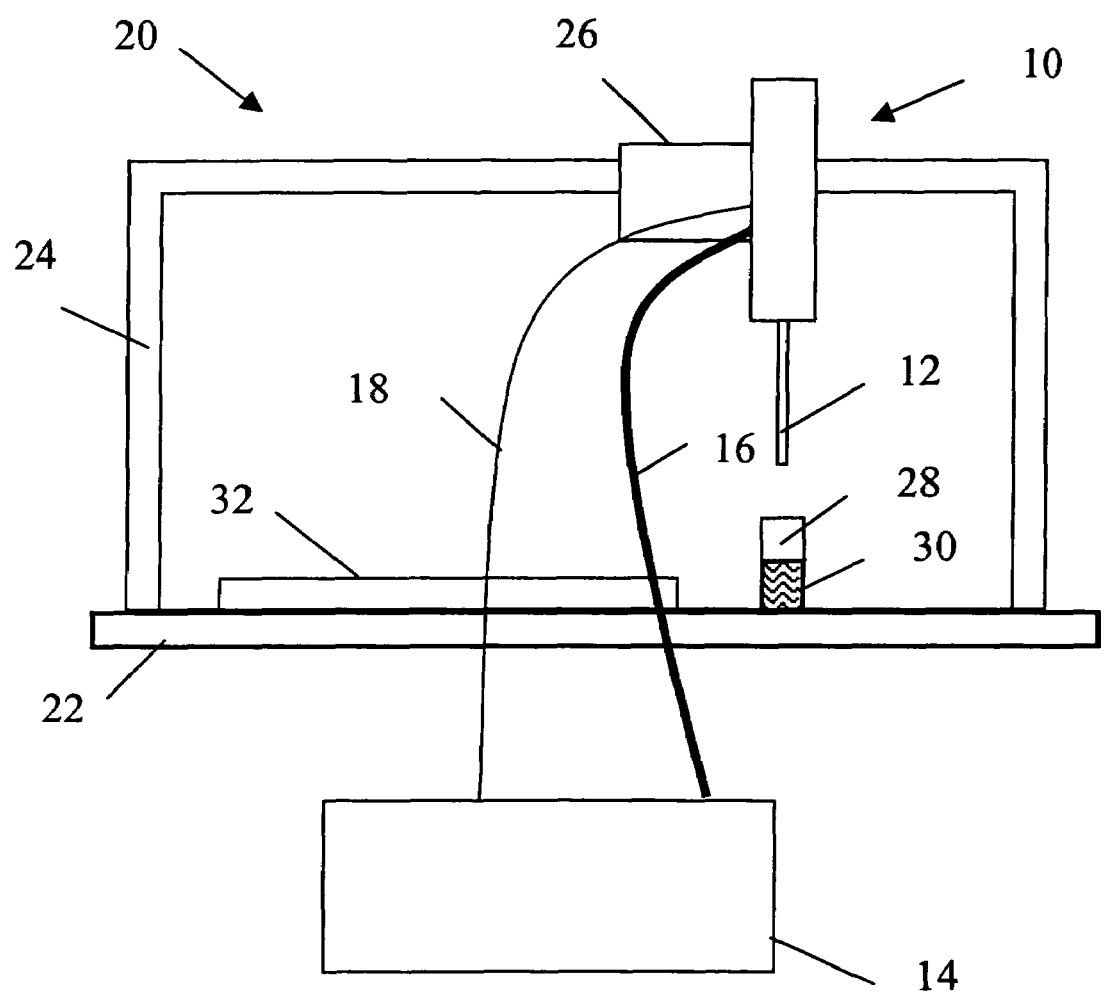

The present invention relates to fluid dispensing devices. It relates more especially to a device intended to deliver very small volumes, typically from 0.001 to a few µl, with great precision.

Such a device is described in U.S. Pat. No. 5,916,524. It comprises a needle for dispensing a fluid into a target and which is connected to an assembly comprising:
- a syringe forming a housing and equipped with a plunger actuated by a stepping motor,
- a tube connecting the syringe to the needle, and
- a set of valves associated with the tube and, initially, allowing the syringe to be filled from a container and then, commanding the flow of the fluid through the tube towards the needle, the amount dispensed being defined by the number of steps effected by the stepping motor.

In most applications, the fluid to be dispensed needs to be very pure. It is therefore expensive and tricky to handle. In addition, the quantities needed may be extremely small. Now, with the device described hereinabove, the liquid passes from the container into the syringe, then from the latter into the needle, through the tube and the valves. The volume thus involved and the risk of contamination are great. Furthermore, it is difficult to control the amount dispensed. This is because the volume of fluid lying between the syringe and the end of the needle is great and can vary appreciably, particularly through deformation of the tube when this tube is flexible.

Another device, which is similar, is described in U.S. Pat. No. 5,927,547. It comprises:
- a dispenser formed of a piezoelectric micro-dosing device,
- a syringe fitted with a plunger and forming a housing, controlled by a stepping motor,
- a pressure sensor, and
- first and second tubes respectively connecting the syringe to the sensor and connecting the sensor to the micro-dosing device.

In this device, the syringe, the sensor and the first tube, together with part of the second tube, contain a transporter liquid. A fluid for dispensing, in this case a liquid also, arranged in a source, is drawn up by the plunger into the micro-dosing device as far as the second tube, with an air bubble interposed between the transporter liquid and the fluid.

The fluid for dispensing is ejected from the micro-dosing device by applying a signal to the piezoelectric part, which generates a shockwave causing a droplet of known volume, dependent on the dimensions of the micro-dosing device and on the characteristics of the fluid concerned, to be emitted.

Control means check, via the sensor, that the pressure of the transport liquid remains constant, thus ensuring correct operation of the micro-dosing device. This pressure is adjusted by sending pulses to the stepping motor, which controls the plunger of the syringe. In order to dispense fluid only into charged targets, the micro-dosing device has a capacitive level sensor at its free end.

The piezoelectric micro-dosing device allows very small volumes, which may be of the order of 5 picolitres, to be delivered. The maximum achievable flow rate is unfortunately limited, which means that the time taken to dispense quantities of fluid of the order of a µl makes such a device somewhat lacking. In addition, the volume available in the micro-dosing device is relatively modest, which means that if excessive numbers of movements between the source and the target are to be avoided, the fluid for dispensing needs to be loaded not only into the micro-dosing device, but also into the tube connecting it to the sensor. There is therefore also a certain risk of contamination.

It should finally be pointed out that the use of a piezoelectric system for commanding the ejection of the fluid for dispensing gives the device a discrete operation which necessarily limits its precision.

Document WO 98/45205 proposes an improved version of the device according to U.S. Pat. No. 5,927,547. In this case, the transporter liquid is displaced by placing its reservoir at a reduced pressure, so that a determined quantity of fluid is drawn up into the piezoelectric micro-dosing device under the control of a flow sensor.

Such a device does, however, still suffer from the use of a piezoelectric dosing device for ejecting the fluid that is to be dispensed.

The object of the present invention is to propose a dispensing device that does not use a piezo micro-dosing device or equivalent element. This object is achieved by virtue of the fact that it comprises:
- a duct for the passage of a transporter liquid,
- a valve fixed to one of its ends,
- a dispensing needle arranged at its other end,
- means of measuring the rate of flow of the transporter liquid in the duct,
- a sealed container containing the transporter liquid and connected to the valve by a tube,
- a pump of the intake and delivery type, in communication with the container and serving to place the latter at a raised pressure or at a reduced pressure so as to cause the liquid to flow through the said duct in one direction or the other, and
- electronic means responding to the said flow measurement means and acting both on the said valve and on the said pump so as to cause a determined amount of fluid to be drawn up into the needle then delivered.

In such a dispensing device, the fluid is drawn up and ejected only under the command of the measuring means of the rate of flow of the transporter liquid, by placing the container of said liquid at a reduced pressure or at a raised pressure. Thus, it is no longer necessary, as it is the case with devices according to documents U.S. Pat. No. 5,927,547 and WO 98/45205, to associate the needle with a piezoelectric system and the high voltage electronic circuit which controls it.

The cost of the device is thus strongly reduced and its reliability is improved. Moreover, the ejection of the fluid by a merely "passive" needle insures a continuous mode of operation whereas the ejection by a piezo is made in a discrete way. The precision is thus improved. Advantageously, the duct is formed inside an elongate body bearing, at its respective ends, the valve and the needle and, in its central portion, the said flow measurement means which are inserted in the path of the duct, in communication therewith. The dispensed volume is thus measured in the optimum way.

For certain applications, in which very small volumes are used, experience has shown that it is advantageous for the duct to be formed inside an elongate body bearing, at its respective ends, the valve and the needle and for the flow measurement means to be inserted in the path of the duct, upstream of the valve.

According to a preferred embodiment, the flow measurement means are of the type that provides a measurement of the pressure difference between two points on the duct and a measurement of the temperature.

In this embodiment, the electronic means may be designed to analyse information from the flow measurement means and to provide information on the conditions of dispensing of the fluid.

The electronic means advantageously comprise:

means of calculating the amount of fluid drawn into or delivered through the needle, on the basis of the information supplied by the flow measurement means, and a control circuit placed under the command of the said calculating means and mainly performing the functions of controlling the pump to place the said container at a raised pressure or at a reduced pressure and of commanding the opening and closing of the valve so as to allow or disallow the displacement of a determined amount of transport liquid in one direction or the other.

As a preference, the calculating means hold, in memory, the values of the viscosity of the transport liquid as a function of temperature and are programmed to calculate, on the basis of the pressure and temperature information delivered by the said flow measurement means, the amount of fluid drawn into or delivered through the needle.

Finally, it is particularly advantageous for the electronic means to be designed, in addition, to detect that a drop of fluid attached to the end of the needle is in contact with a target.

It is useful to note that the device as described hereinabove makes it possible precisely to measure the volume of fluid both when it is drawn up and when it is dispensed. It is thus possible to prepare doses of one or several fluids, separated by an air bubble, these doses then being dispensed into the targets.

Figure 2:
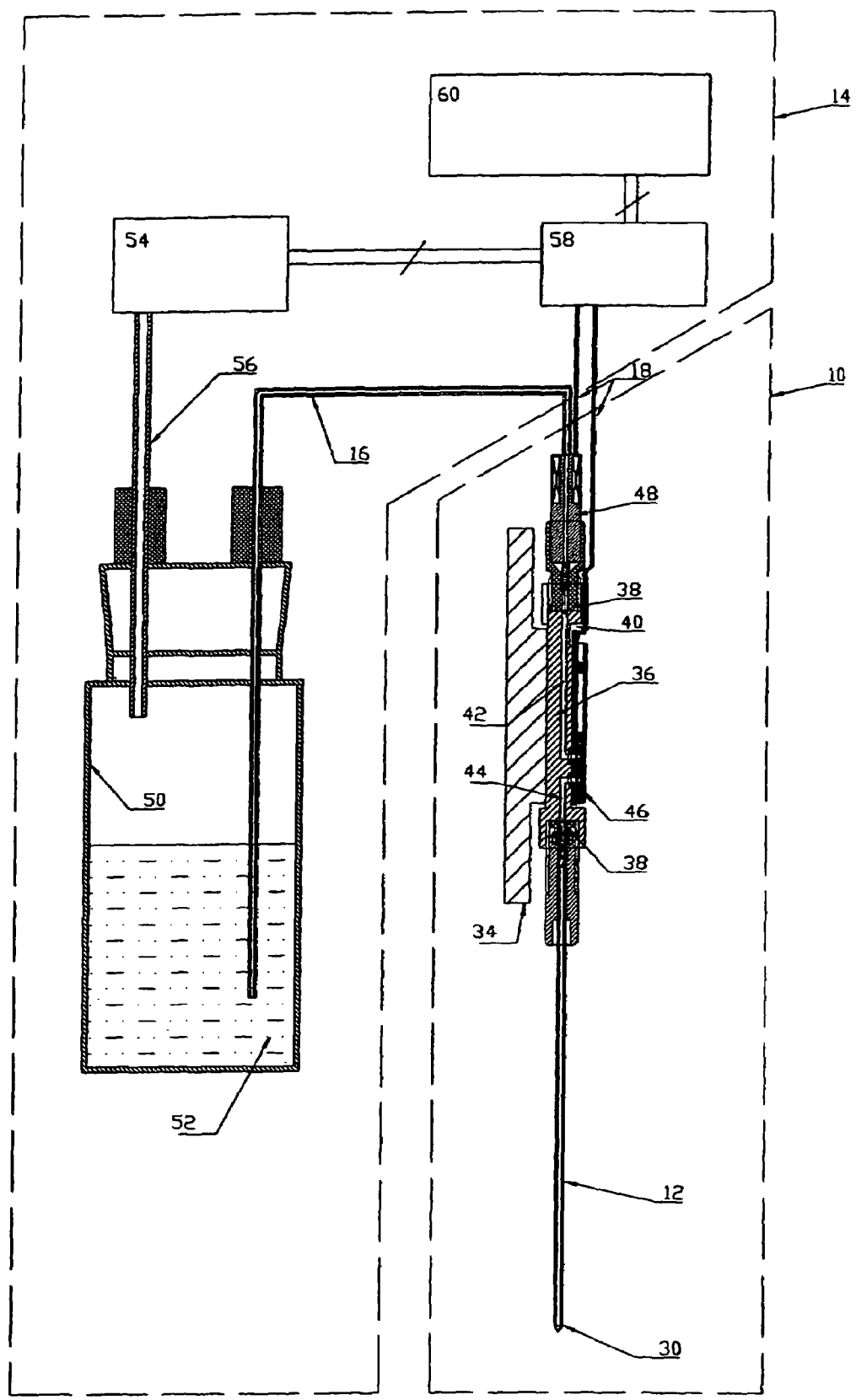

Other advantages and features of the invention will become apparent from the description which will follow, given with respect to the appended drawing, in which:

FIG. 1 is the operating diagram of a fluid dispensing device in its surroundings, and FIG. 2 shows, in greater detail, the structure of the device according to the invention.

FIG. 1 shows, schematically, an assembly comprising a fluid dispenser 10 equipped with a dispensing needle 12 and a control cabinet 14. A tube 16 and a cable 18 connect the dispenser 10 to the cabinet 14.

The assembly further comprises a robot 20 of the Cartesian type, formed of a horizontal table 22, of a portal frame 24 mounted so that it can move in translation over the table in a direction perpendicular to the plane of the figure, and of a carriage 26 mounted so that it can move in horizontal translation along the portal frame in a direction parallel to the plane of the figure. The dispenser 10 is mounted so that it can move in vertical translation on the carriage 26, so that it can thus move along three mutually orthogonal axes. A source 28 containing a fluid 30 and a target 32 are arranged on the table 22, in the space swept by the portal frame 24.

The assembly depicted in FIG. 1 is intended to allow precise transfer of the fluid 30, by means of the dispenser 10, from the source 28 to the target 32.

Both the source 28 and the target 32 may be a test specimen, a microtitration plate (of type 96, 384 or 1536 for example) or any other surface or reservoir of liquid arranged in any spatial format whatsoever. The fluid 30 is generally a liquid, but could just as easily be a gas. In this case, the source 28 is a sealed container closed by a membrane able to be perforated and the needle 12 is of a type similar to those used for hypodermic injections, for example.

Reference will now be made to FIG. 2 which, in greater detail, shows the dispenser 10 and the control cabinet 14.

The dispenser 10 comprises a support 34 intended to be fitted to the carriage 26 and bearing an elongate body 36, advantageously made of chemically inert plastic, such as the material known by the name of PEEK, of cylindrical overall shape and mounted vertically. At each end it has a cylindrical housing 38 and, in its central portion, it has a cavity 40. It is also pierced, along its axis, with an upper duct 42 opening, on the one hand, into the upper housing 38 and, on the other hand, into the cavity 40 and with a lower duct 44 opening, on the one hand, into the lower housing 38 and, on the other hand, into the cavity 40.

The cavity 40 houses a flow meter 46, made on a ceramic tablet and which is positioned in such a way as to find itself in sealed communication with the ends of the ducts 42 and 44. It is advantageously fixed by clamping, with the insertion of seals.

The upper housing 38 houses, in a sealed and removable manner, via an appropriate adapter, a valve 48 the function of which is to place the upper duct 42 in communication with the tube 16.

At the other end of the body 36, the lower housing 38 houses, also in a sealed and removable manner, via an appropriate adapter, the end of the dispensing needle 12.

The needle 12 is chosen according to the way in which the fluid 30 is to be dispensed to the target 32 and according to the volume to be dispensed, as will be specified later on.

The material of which the needle 12 is made must not react with the fluid. Stainless steel may, for example, be used in many cases. The basic material may or may not be covered with a layer improving the wettability or non-wettability properties of certain internal or external surfaces of the needle.

The length and the bore of the needle 12 are chosen according to the quantity of fluid to be dispensed to the target 32 in one or more shots. These dimensions are defined in such a way that the volume of the bore of the needle is greater than the volume of fluid to be dispensed in a single shot. It is thus possible for the volume in question to be drawn up in such a way that it is entirely housed in the needle, something which affords various advantages.

Specifically, once the fluid 30 can remain confined to the needle 12, when there is a wish to dispense another fluid, all that is required is for this needle to be changed rather than for the whole dispenser to have to be cleaned. It is thus possible, during one and the same sequence, to dispense several fluids, in highly varying quantities, without that posing any problem. To do this, all that is required is for the needle to be changed, something that a robot can do with no difficulty.

It is also possible to dispense highly corrosive fluids, simply by choosing an appropriate needle.

In other words, these advantages stem from the fact that there is no interference between the fluid or fluids for dispensing and the components of the dispenser 10 other than the needle 12.

The flow meter 46 plays an important part in the correct operation of the device because it needs to be able, precisely, to measure a volume of a few nanolitres. It is advantageous for this purpose to use the flow meter described in the publication entitled "A Differential Pressure Liquid Flow Sensor for Flow Regulation and Dosing Systems" by M. A. Boillat et al. 0-7803-2503-6© 1995 IEEE. This flow meter comprises sensors making it possible to measure a pressure difference between its inlet and its outlet, and the temperature of the fluid passing through it. Once these two parameters have been determined, it is possible to calculate the flow rate, provided that the viscosity of the transport liquid as a function of its temperature is known.

As FIG. 2 shows, the control cabinet 14 comprises a sealed container 50 partially filled with a transport liquid 52 into which the tube 16 connected to the valve 48 dips. A pump 54, of the intake and delivery type, is in communication, via a duct 56, with the upper part of the container situated above the liquid 52.

The liquid 52 is chosen according to the fluid 30 for dispensing so that these liquids are, from the chemical point of view, neutral with respect to each other. It will be noted that the liquid 52 fills the tube 16 and passes through the dispenser 10 as far as the needle 12, as will be specified later on.

The pump 54 allows the container 50 to be placed at a raised pressure or at a reduced pressure. In that way, when the valve 48 is opened, the liquid 52 can be displaced from the container 50 to the needle 12 or in the other direction.

A control circuit 58 is connected to the pump 54, to the valve 48 and to the flow meter 46. It is under the command of a computer 60 to perform the following main functions:
- controlling the pump 54 with a view to placing the container 50 at a raised pressure or at a reduced pressure,
- commanding the opening and closing of the valve 48 allowing or disallowing the displacement of the liquid 52 in one direction or the other,
- transmitting to the computer 60 the pressure and temperature measurements from the flow meter 46.

The computer 60 serves to program and coordinate the assembly. It thus controls the movements of the robot 20 to cause the dispenser 10 to go and find doses of fluid 30 from the source 28 and deposit them on the target 32. In addition, it holds in its memory the values of the viscosity of the transport liquid as a function of temperature. That allows it, on the basis of the pressure and temperature information delivered by the flow meter 46, to determine, precisely and in real time, the amount of fluid drawn up into or delivered through the needle 12. It is thus possible to retain in memory the exact quantities of fluid 30 dispensed each time. Furthermore, analysis of the signals emitted by the flow meter 46 makes it possible to detect malfunctions in the device, such as sealing problems or problems of blockages in the ducts 42 or 44.

The device which has just been described allows a fluid 30 to be transferred between the source 28 and the target 32 in a particularly effective and economical way. This operation is performed as follows.

First of all, the transporter liquid 52 is introduced into the container 50. The latter is then closed and the pump 54 is activated, so as to place the container 46 at a raised pressure. The valve 48 is then opened, so that the liquid 52 enters the tube 16 and passes through the dispenser 10 as far as the needle 12 which it completely fills. The valve 48 is then closed.

During this operation it is essential to make sure that no air bubbles remain trapped in the tube 16, as this would degrade the performance of the device. This check can be done automatically, by analysing the signals emitted by the flow meter. Indeed it is found that the presence of air bubbles leads to elasticity in the ducts 42 and 44, and this slows the pressure rise when the valve is open.

The device 10 is now ready to take fluid 30 from the source 28 to deliver it to the target 32. For this, the container 50 is placed at a reduced pressure by the pump 54 and the robot 20 brings the needle 12 over the source 28.

According to an advantageous mode of operation, a small amount of air is first of all drawn up by the needle 12 so as to form a bubble between the liquid 52 and the fluid 30 for dispensing. For this, the valve 48 is opened and the liquid 52 rises up in the needle 12 towards the container 50, through the flow meter 46 whose output signal allows the control circuit 58 to calculate the volume of air drawn in, that is to say the volume of the bubble. When the measured volume reaches the desired value contained in the computer 60, the valve 48 is closed and the robot 20 introduces the needle 12 into the fluid 30.

When the latter is a liquid, which it generally is, the flow meter 46 records a sudden variation in pressure when the needle 12 goes in. The computer 60 can thus determine the position of the needle 12 with respect to the surface of the fluid 30. It then gives the robot 20 the order to plunge the needle 12 into the fluid 30 far enough to avoid the formation of parasitic bubbles during suction. The valve is then opened again so that the drawing-up operation can begin.

When, on the basis of the information supplied by the flow meter 46, the computer 60 determines that the desired amount of fluid has been drawn up into the needle 12, the valve 48 is closed again.

It is possible to repeat this operation several times so that the needle 12 can contain several doses of fluid 30, each separated by an air bubble.

As an alternative, the fluid 30 can be drawn up without the interposition of an air bubble. The needle 12 is then plunged directly into the fluid 26 and the drawn-up volume is determined as described above, but in a single shot.

When the needle 12 is filled with the fluid for dispensing, the robot 20 takes the dispenser 10 over the target 32 and the pump 54 places the container 50 at a raised pressure. The valve 48 is then opened to allow the fluid to be ejected and closed again when the measured volume corresponds to the volume set by the computer.

The dimensions of the needle bore play an important part, especially when the end of this needle is in the air. In this case, precise dispensing can be achieved only if the fluid 30 flows out uniformly. What this amounts to is that it is necessary to avoid drops forming during the dispensing operation. A suitable choice of the pressure in the container 50 and of the bore at the free end of the needle 12 allows satisfactory operation to be ensured.

When a small volume needs to be dispensed, it is advantageous to use a needle having a narrowing of the hole at its free end, this being well known by the term "nozzle". It is also advantageous for the flow meter 46 to be upstream of the valve 48. Indeed, experience has shown that the flow can be well controlled in this way, even with low flow rates.

It goes without saying that the device according to the invention can be used in yet other conditions. It is thus also possible to dispense a gas. In this case, the needle is introduced into a sealed bottle, in place of the source 24, which contains the gas and the liquid. A volume of gas is drawn up, as explained above with regard to the air, followed by a drop of liquid, so that the gas is trapped in the needle by successive bubbles of tailored volume. This gas is then dispensed into a target by injecting into it a volume corresponding to the volume of the gas and of the drop separating two successive bubbles.

The invention claimed is:

1. Fluid dispensing device characterized in that it comprises:
    a dispensing member (10) comprising:
        a duct (42, 44) for the passage of a transporter liquid (52), a valve (48) fixed to one of the ends (38) of the said duct, a passive dispensing needle (12) arranged at the other end (38), and means (46) of measuring the rate of flow of the transporter liquid (52) in the duct, inserted between said valve and said needle;

a sealed container (50) containing the transporter liquid (52) and connected to the valve (48) by a tube, a pump (54) of the intake and delivery type, in communication with the container (50) and serving to place the latter at a raised pressure or at a reduced pressure so as to cause the transporter liquid (52) to flow through the said duct (42, 44) in one direction or the other, and electronic means (58, 60) responding to the said measurement means (46) and acting both on the said valve (48) and on the said pump (54) so as to cause a determined amount of fluid (30) to be drawn up into the needle (12) to be dispensed, means (60) of calculating the amount of fluid drawn into or delivered through the needle, on the basis of the information supplied by the flow measurement means, and a control circuit (58) placed under the command of the said calculating means (60) and mainly performing the functions of controlling the pump (54) to place the said container (50) at a raised pressure or at a reduced pressure and of commanding the opening and closing of the valve (48) so as to allow or disallow the displacement of a determined amount of transport liquid (52) in one direction or the other, said displacement causing a determined amount of fluid (30) to be drawn into said needle (12) to be dispensed.

2. Fluid dispensing device according to claim 1, characterized in that the said duct (42, 44) is formed inside an elongate body (36) bearing, at its respective ends (38), the said valve (48) and the said needle (12) and, in its central portion (40), the said flow measurement means (46) which are inserted in the path of the duct (42, 44), in communication therewith.

3. Fluid dispensing device according to claim 1, characterized in that the said duct (42, 44) is formed inside an elongate body (36) bearing, at its respective ends (38), the said valve (48) and the said needle (12), and in that the said flow measurement means are inserted in the path of the duct (42) upstream of the said valve (48), in communication with this duct.

4. Fluid dispensing device according to claim 1, characterized in that the said flow measurement means (46) are of the type that provides a measurement of the pressure difference between two points on the duct and a measurement of the temperature.

5. Fluid dispensing device according to claim 4, characterized in that the said electronic means (58, 60) are designed to analyse information from the flow measurement means (46) and to provide information on the conditions of dispensing of the said fluid.

6. Fluid dispensing device according to claim 1 characterized in that the said calculating means (60) hold, in memory, the values of the viscosity of the transport liquid (52) as a function of temperature and are programmed to calculate, on the basis of the pressure and temperature information delivered by the said flow measurement means (46), the amount of fluid drawn into or delivered through the needle (12).

* * * * *